United States Patent [19]

Augustine

[11] Patent Number: 4,832,020
[45] Date of Patent: May 23, 1989

[54] TRACHEAL INTUBATION GUIDE

[76] Inventor: Scott D. Augustine, 1601 Stonecrest Ct., Blue Springs, Mo. 64015

[21] Appl. No.: 126,567

[22] Filed: Nov. 30, 1987

Related U.S. Application Data

[63] Continuation-in-part of Ser. No. 30,697, Mar. 24, 1987, abandoned.

[51] Int. Cl.$^4$ ............................................. A61M 16/00
[52] U.S. Cl. .................................. 128/207.14; 128/10
[58] Field of Search ....................... 128/200.26, 207.14, 128/10, 207.15

[56] References Cited

U.S. PATENT DOCUMENTS

| | | | |
|---|---|---|---|
| 2,354,471 | 7/1944 | MacIntosh | 128/10 |
| 3,802,440 | 4/1974 | Salem et al. | 128/351 |
| 3,986,854 | 10/1976 | Scrivo et al. | 128/16 |
| 4,067,331 | 1/1978 | Berman | 128/200.26 |
| 4,356,821 | 11/1982 | Rind | 128/207.14 |
| 4,432,351 | 2/1984 | Hoary | 128/3 |
| 4,612,927 | 9/1986 | Krüger | 128/200.26 |
| 4,669,463 | 6/1987 | McConnell | 128/207.14 |
| 4,712,536 | 12/1987 | Hawks | 128/3 |
| 4,713,053 | 12/1987 | Lee | 604/264 |

Primary Examiner—Edward M. Coven
Assistant Examiner—John P. Lacyk
Attorney, Agent, or Firm—Baker, Maxham, Jester & Meador

[57] ABSTRACT

A tracheal intubation guide comprises a tubular member having a curved forward end shaped to follow the curvature of the back of the tongue and throat of a patient, and a rear end for projecting out through the mouth of the patient, and an anterior guide surface extending along at least part of the length of the member to its forward end for guiding the member into the throat into a position opposite the opening into the larynx. The tubular member has a through bore for holding an endotracheal tube, and the guide surface has a forward edge of concave shape for engaging the front of the epiglottis and seating over the hyo-epiglottic ligament when the member is accurately positioned. Correct positioning can be detected by external palpation of the neck.

18 Claims, 3 Drawing Sheets

TRACHEAL INTUBATION GUIDE

This is a continuation-in-part of Ser. No. 07/030,697 filed Mar. 24, 1987 which is now abandoned.

BACKGROUND OF THE INVENTION

The present invention relates to a guide for assisting medical personnel in inserting an endotracheal tube into the trachea, or windpipe, of a patient.

Endotracheal intubation is the technique of inserting a tube into the trachea of a patient in order to aid in or permit respiration. It is commonly used in surgery and in emergency care situations, for example in the case of trauma or cardiac arrest victims suffering from breathing difficulties. Various other techniques for securing an airway are known, such as the esophageal obturator airway, the esophageal gastric tube airway, and the pharyngeal tracheal lumen airway, as well as mouth to mouth or bag and mask respiration. However, none of these places an airway into the trachea and thus none of them will truly secure the airway to prevent potential aspiration of blood, vomitus, or other foreign material into the lungs. Additionally, some of these techniques can induce major additional trauma in the patient.

Thus endotracheal intubation is generally considered to be the superior method of securing an airway and assuring adequate ventilation. However, one problem with this technique is that it requires significant operator skill and experience. Unskilled insertion can cause additional injuries, for example to the front incisors. Another problem is that many existing techniques for inserting a tube into the trachea require special positioning of the patient's head, and thus cannot be done with trauma victims until cervical spine fractures have been ruled out, because of the possibility of additional spinal cord damage.

A laryngoscope is commonly used to aid in placing of an endotracheal tube. This allows the operator to observe the insertion of the tube, but requires that the patient be positioned with their head tilted back, which is not normally possible with trauma victims. Visualization of the larynx may be impossible if the pharynx is filled with blood or vomitus. Laryngoscopes are relatively difficult instruments to handle, even for skilled medical personnel. Thus they are not normally suitable for use by paramedical personnel in the field.

Other endotracheal intubation techniques involve the insertion of the tube "blind" or by feel. Some devices have been proposed in the past for aiding in "blind" insertion of an endotracheal tube. U.S. Pat. No. 4,612,927 of Kruger, for example, shows an instrument of open channel section terminating in a head having a central concavity for engaging the rear of the larynx. A tube can then be guided along the channel and directed into the trachea via a suitable ramp adjacent the head of the instrument. U.S. Pat. Nos. 4,054,135, 4,068,658, 4,067,331 and 4,069,820 of Berman all show a pharyngeal airway for intubation which has a distal tip for engaging the epiglottis to direct a tube into the trachea.

SUMMARY OF THE INVENTION

It is an object of the present invention to provide an improved guide for endotracheal intubation, which can permit medical personnel, with suitable training, to insert a tube into the trachea relatively easily.

According to the present invention an endotracheal intubation guide is provided which comprises a tubular member having a curved forward end shaped to follow the curvature of the back of the tongue and anterior surface of the throat of a patient and a rear end for projecting out through the mouth of the patient, and an anterior guide surface which extends along at least part of the length of the tubular member to its forward end and is of equivalent curvature, for guiding the tubular member into the mouth and throat of a patient. The guide surface has a forward edge of concave shape for engaging the front of the epiglottis and for seating over the hyo-epiglottic ligament to position the tubular member opposite the opening to the larynx. When the guide has been inserted through a patient's mouth until the front edge of the guide surface is accurately seated, an endotracheal tube previously inserted through the tubular member towards its forward end can be advanced into the trachea.

Accurate positioning of the guide can be detected by external palpation of the neck of the patient. The epiglottis is a shield-shaped cartilage which rises above the opening to the windpipe or larynx. The epiglottis is anchored anteriorly to the hyoid bone in its midline by the hyo-epiglottic ligament. The hyoid bone is the highest bone palpable on the anterior aspect of the neck, and is a U-shaped structure which surrounds and suspends the larynx (the upper end of the windpipe). The epiglottis is always on the anterior, superior aspect of the larynx, and the guide of this invention uses this relationship to establish accurate positioning of an endotracheal tube.

According to another aspect of the present invention, a method of inserting an endotracheal tube comprises the steps of first inserting the endotracheal tube from the rear to the forward end of the intubation guide. The guide is then inserted through the mouth and throat of the patient. The guide surface travels over the tongue and anterior surface of the throat until its forward edge engages the front of the epiglottis. Accurate, central positioning of the guide surface can be detected by external palpation of the neck at and above the hyoid bone. If the guide is not accurately positioned with the concave edge centrally seated on the ligament in the midline, a lateral edge of the guide would be palpable on one or the other side of the neck above the hyoid bone, requiring re-positioning of the guide. Accurate midline positioning with the concave edge of the guide surface seated on the hyo-epiglottic ligament can be detected by lateral movements of the guide which will be detected externally as a generalized movement of the hyoid bone, felt by palpation of the neck in the area of the bone. Once accurate positioning is detected, anterior elevation of the tongue will tension the hyo-epiglottic ligament and elevate the epiglottis anteriorly, opening the larynx immediately posterior to the epiglottis. The guide tube member will then be positioned with its open forward end directly opposing the opening to the larynx. The endotracheal tube can then be advanced through the forward end of the guide member and into the larynx and trachea. At this point the guide can be removed, leaving the endotracheal tube in place.

The anterior guide surface may be formed integrally with the tubular guide member or may be a generally flat, J-shaped member secured to the anterior surface of the tubular member. The forward edge of the guide surface preferably projects forwardly of the open forward end of the tubular member. In a first embodiment of the invention a pair of rollers are mounted at the forward edge of the guide surface, and the concave shape is defined by the opposed faces of the rollers which are designed to seat around the hyo-epiglottic ligament when the guide is accurately positioned. The rollers aid in sliding the guide over the rear of the tongue of a patient, which can be sticky in some patients. Additional rollers may be provided along the curved portion of the guide surface to facilitate sliding movement of the tracheal intubation guide. In a second embodiment of the invention, the guide surface is smooth and unbroken with the concave shape at the forward edge of the guide surface being defined by a pair of curved projections which are designed to seat around the hyo-epiglottic ligament. In the second embodiment, the guide slides adequately over the rear of the patient's tongue.

The tubular member itself preferably has portions of open section to aid in removal of the guide once an endotracheal tube has been inserted. The open portions are preferably provided by a continuous, serpentine cut-out extending along the length of the tube which is designed so that an endotracheal tube will be kept within the tubular member during positioning but allows the guide to easily removed once the tube is advanced into the trachea. A suitable handle may be provided at the rear end of the guide for holding by an operator while inserting the guide, and a thumb indent may be provided on the handle to ensure alignment of the tubular member with the operator's hand, which assists in accurate positioning of the guide on insertion.

The tracheal intubation guide and method of this invention will aid in accurate intubation of the trachea, increasing the reliability and safety of this procedure. It is particularly useful in the case of trauma or other emergency victims, where use of a laryngoscope may not be possible, since it does not require movement of the head, or visualization of the larynx.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which.

DESCRIPTION OF THE PREFERRED EMBODIMENT

Figure 1:
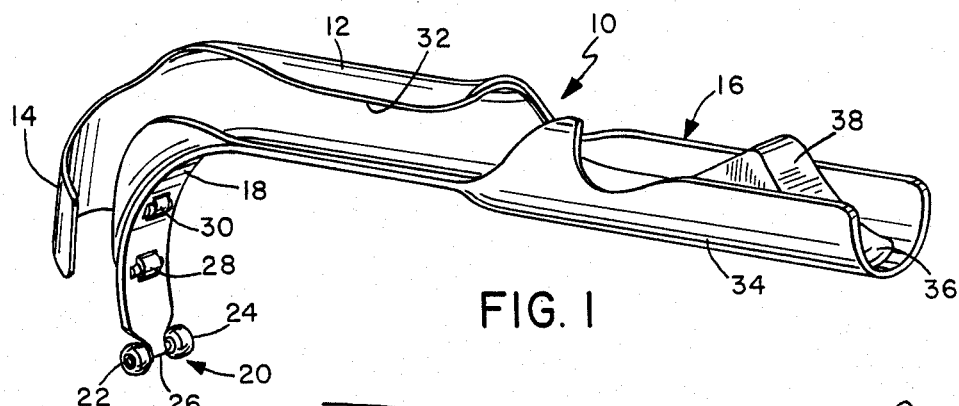
FIG. 1 is a perspective view of a tracheal intubation guide according to a first embodiment of the invention.
Figure 2:
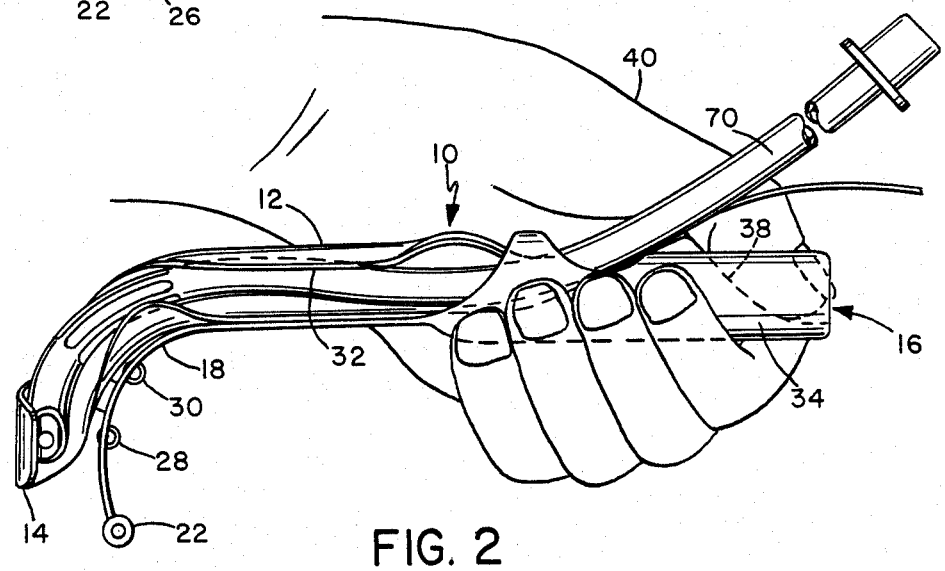
FIG. 2 is a side elevation view of the first embodiment guide with an endotracheal tube inserted and showing the method of holding the guide.

FIGS. 1 and 2 of the drawings show a tracheal intubation guide 10 according to a first embodiment of the present invention. The guide 10 basically comprises a tubular member or guide tube 12 having a curved forward end 14 and a generally straight rear end 16, an underside 17, and an anterior guide surface 18 extending along at least part of the length of the underside of the tubular member and beyond the tubular member's forward end. The guide surface 18 may be formed integrally with the tubular member or may be suitably attached to the anterior surface of member 12, and is suitably a generally flattened J-shaped strip as seen in FIGS. 1 and 2. In one example the strip was approximately ¾ inch wide, although other dimensions may be appropiate for different age patients.

As can be seen in FIG. 1, the forward edge 20 of the guide surface 18 is of generally concave shape, the concave shape in the first embodiment being defined between a pair of rollers or wheels 22, 24 which have suitably inclined opposing faces to define a concave shape or indent 26. The rollers 22, 24 are preferably of rounded, ball-like shape as shown in FIG. 1. An additional pair of rollers 28, 30 are provided along the curved portion of the guide surface 18.

The tubular member 12 has open portions along its length, and in the first embodiment of the invention member 12 has a serpentine slot or cutout 32 extending along it. A suitable handle 34 is provided at the rear end of member 12 for holding of the guide by an operator as illustrated in FIG. 2. The handle has a suitable thumb indent 36 comprising a ramped surface 38 at its outer end for positioning of the operator's thumb 40 while holding the guide as shown in FIG. 2. This ensures that the guide 10 is aligned with the operator's hand during insertion. The guide 10 is preferably held by the operator in a similar manner to a traditional laryngoscope, with the operator positioned at the patient's head.

The guide is rigid, and may be of any suitable non-toxic material such as a plastics material. The curvature of the forward end of the guide is designed to follow the general curvature of the back of the tongue and anterior surface of the throat, as explained below.

Figure 5:
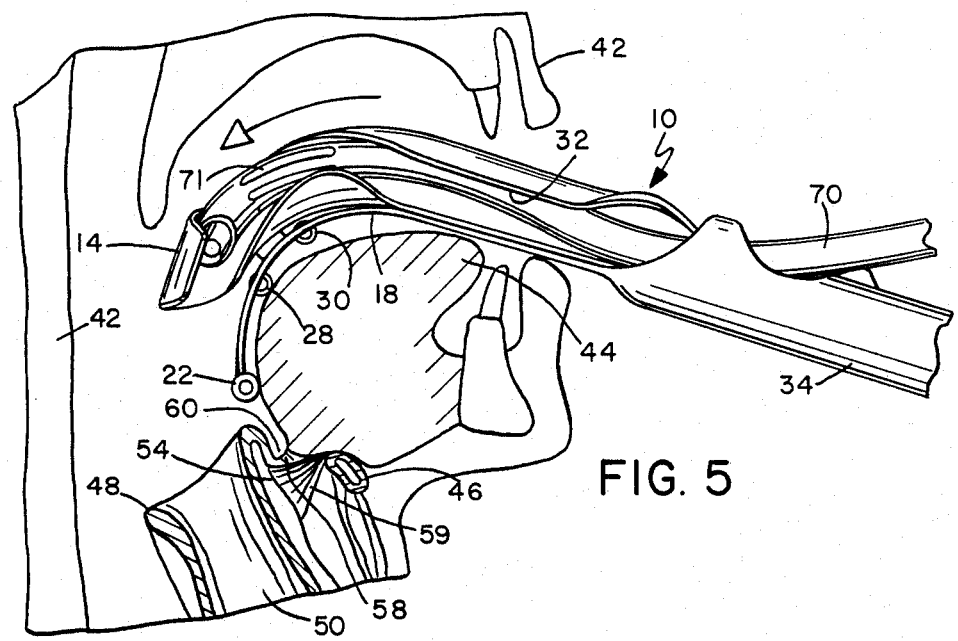
FIG. 5 is a cut away view of a mouth and throat area, showing insertion of the first embodiment guide.
Figure 6:
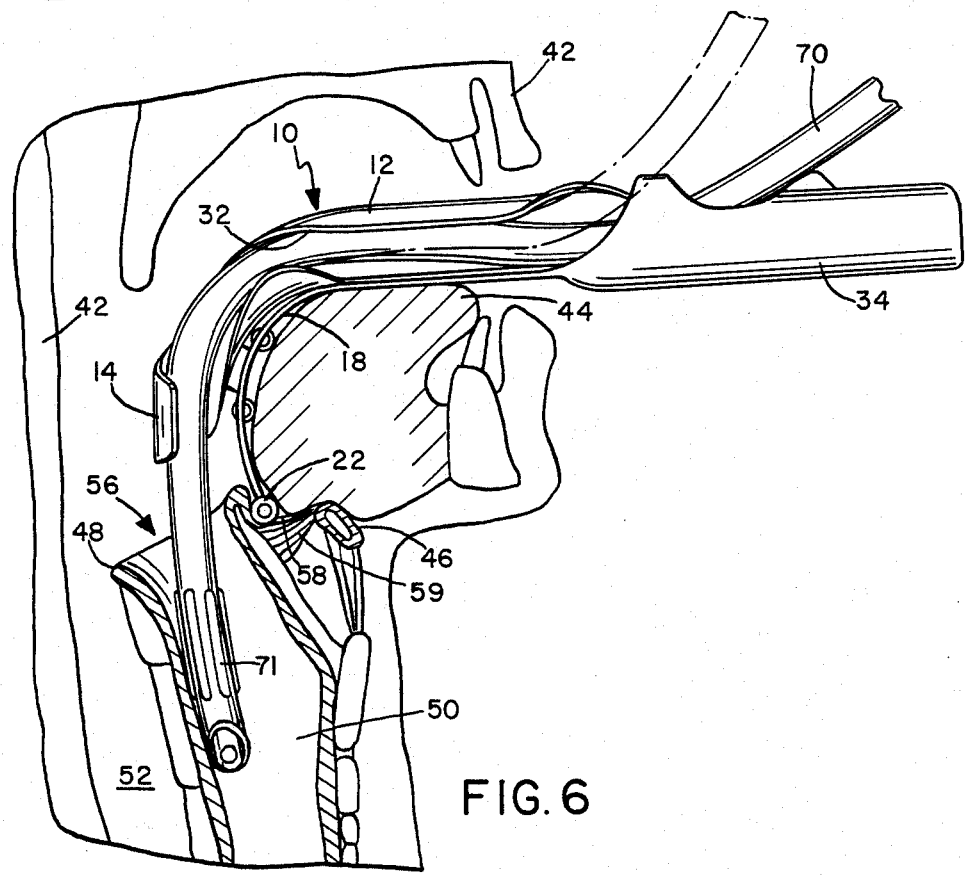
FIG. 6 is a similar view with the end of the first embodiment guide seated over the hyo-epiglottic ligament and the endotracheal tube inserted through the first embodiment guide into the trachea.

The method of inserting an endotracheal tube using the tracheal intubation guide according to the principles of the invention will best be understood with reference to FIGS. 5 and 6 of the drawings, which show a partial section through the head 42 of a patient. As shown in FIGS. 5 and 6, the tongue 44 curves downwardly at the back of the throat where the root of the tongue is anchored to the hyoid bone 46. The hyoid bone is a U-shaped structure which lies horizontally and opens rearwardly, and which surrounds and suspends the larynx 48. The larynx 48 is the upper end of the windpipe, or trachea 50. To the rear of the trachea is the esophagus 52 through which food and drink enters the stomach. The epiglottis 54 is a shield-shaped cartilage which rises above the glottis 56, or opening to the windpipe, and which protects the larynx. When food and drink is passed over the tongue towards the windpipe, it is deflected around the lateral aspects of the glottis and is thus prevented from entering the larynx, which is also protected by the reflex closure of the vocal cords. The epiglottis 54 is anchored anteriorly to the hyoid bone via the hyo-epiglottic ligament 59. The depression 58 which is bounded anteriorly by the tongue, posteriorly by the epiglottis and inferiorly by the hyo-epiglottic ligament is known as the vallecula. In a coronal section, the depression 58 assumes a convex contour between the epiglottis and the hyoid bone over the hyo-epiglottic ligament. Anterior traction at the base of the tongue moves the hyoid bone anteriorly, which tensions the hyo-epiglottic ligament and thus elevates the epiglottis forwardly and off the glottis to expose the opening to the larynx.

Figure 3:
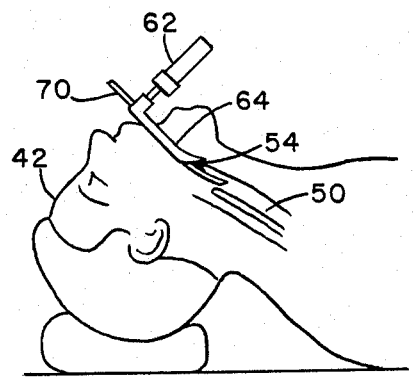
FIG. 3 illustrates a prior art method of inserting an endotracheal tube with the head tilted back.

Before describing the technique of inserting an endotracheal tube according to this invention, reference is first made to FIG. 3 which illustrates a prior art technique using a laryngoscope 62 for direct observation of the tube insertion. The laryngoscope 62 must first be inserted as shown in FIG. 3, requiring the patient's head to be tilted back. In view of the risk of additional spinal cord injury resulting from such head movement, this technique is not normally used for trauma victims. the tip of the laryngoscope blade 64 elevates the epiglottis.

The guide of the invention allows relatively accurate, "blind" insertion of an endotracheal tube without needing to tilt or move a patient's head. As illustrated by use of the first embodiment of the guide illustrated in FIGS. 1 and 2, before insertion of the guide, an endotracheal tube 70 having a cuff 71 adjacent its forward end is first inserted from the rear to the forward end of tubular member 12, into the position shown in FIG. 4. With the head in the position shown FIG. 4, the mouth is opened and the forward end of the guide is inserted through the mouth, as indicated by the arrow in FIG. 5. The guide surface slides over the tongue surface into the throat, assisted by the rollers which ensure relatively smooth movement even in cases where the tongue surface is sticky. The guide is inserted into the throat by the operator gripping the handle as shown in FIG. 2, until the forward edge of the guide surface engages the front of the epiglottis as shown in FIG. 6. As can be seen in FIG. 6, the curvature of the guide tube and anterior guide surface is designed to follow the curvature of the back of the tongue into the throat.

If the guide is centrally positioned, the concave indent at the forward edge of the guide surface will seat or fit over the convex contour of the hyo-epiglottic ligament, as shown in FIG. 6, with one of the rollers on each side of the ligament. Correct positioning can be detected by external palpation of the sides of the neck in the region of the hyoid bone. If the guide is not accurately seated on the ligament, a lateral edge of the guide will be felt on one side of the neck above the hyoid bone. In that case the guide is partially withdrawn and then re-inserted. When the guide is accurately seated, lateral movement of the guide will result in a generalized movement of the hyoid bone, which can be detected by external palpation of the neck.

Once accurate positioning of the guide has been detected, anterior elevation of the tongue will tension the hyo-epiglottis ligament and elevate the epiglottis anteriorly, as indicated in FIG. 6, opening the larynx immediately behind the epiglottis. The guide is designed so that when the epiglottis is elevated, the open forward end of the guide tube and the end of the previously inserted endotracheal tube will be positioned directly opposite the opening into the trachea, as shown in FIG. 6.

The epiglottis may be elevated by elevation of the tongue. However, the guide may itself include an epiglottic elevating ramp (not shown in the drawings) in an alternative embodiment, although this is not essential for proper functioning of the guide. The ramp may suitably comprise a one-inch member hinged to the rear of the guide surface approximately one inch from its forward edge and designed to hang down at a 45-degree angle during insertion of the guide. The ramp will be connected to a lever on the handle. When the guide has been positioned, the lever may be used to elevate the ramp anteriorly and pinch the epiglottis between the ramp and rear of the guide surface. This would show that the epiglottis had been located and would also ensure maximum opening of the larynx.

Once accurate positioning of the guide has been assured and the epiglottis has been elevated, the endotracheal tube 70 is advanced through the tubular member 12 as shown in FIG. 6, which guides it down through the larynx and into the trachea. Once the tube 70 has been inserted fully, cuff 71 is inflated to hold the tube in place and the guide can be removed leaving the tube in place. The open section, serpentine groove in the tubular guide member will keep the tube within the member 12 during positioning but allows the guide 10 to be removed easily without dislodging the tube 70 once the tube has been inserted, as indicated by the dotted lines in FIG. 6. Once tube 70 is moved to the position shown in dotted lines, the guide 10 can be easily withdrawn.

Figure 4:
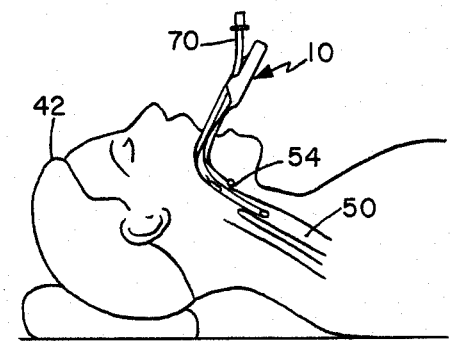
FIG. 4 illustrates the method of inserting an endotracheal tube according to the principles of the invention.

Although in the method described above an endotracheal tube is positioned in the tubular member prior to insertion into the throat in view of the open, serpentine cut-out, it may alternatively be positioned after the guide 10 has been inserted, depending on the shape and position of the serpentine cut-out. For example, the intubation guide may be designed to have an opening in its posterior surface at the forward end, facing the nasal pharynx, to allow entry of a nasally inserted endotracheal tube into the guide member 12, for final guiding of the endotracheal tube into the trachea. However, the insertion technique will normally be via the mouth as indicated in FIGS. 4 to 6.

Figure 7:
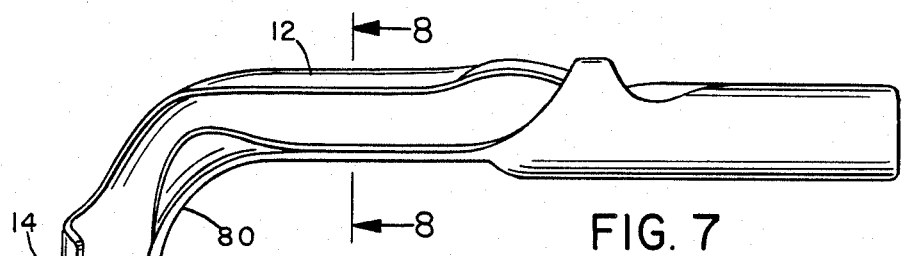
FIG. 7 is a perspective view of a tracheal intubation guide according to a second embodiment of the invention.
Figure 9:
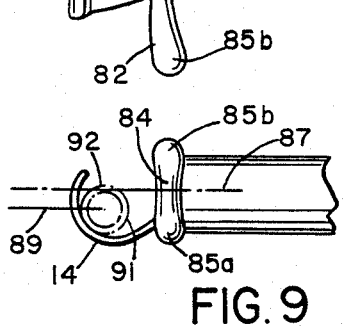
FIG. 9 is an end view of FIG. 7, rotated by 90° to illustrate the alignment of the forward end with the anterior guide surface.
Figure 8:
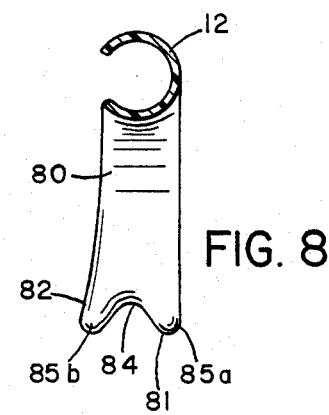
FIG. 8 is a sectional view showing the profile of the anterior guide surface of the second embodiment.
Figure 10:
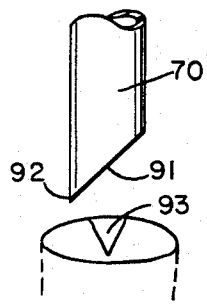
FIG. 10 is a schematic illustration of the alignment of the beveled tip of an endotracheal tube without an offset between the center lines of the forward end and the anterior guide surface.
Figure 11:
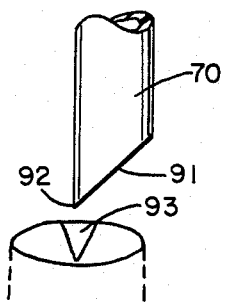
FIG. 11 is a schematic illustration of the alignment of the beveled tip when the center lines are offset.

A second embodiment of the guide is illustrated in FIGS. 7–9. The second embodiment is characterized primarily in that the anterior guide surface has a smooth, continuous surface unbroken by the rollers of the first embodiment. Thus, as with the first embodiment, the guide surface is attached to the underside of the through bore and extends beyond the curved forward end 14 of the guide tube 12. the guide surface of the second embodiment is indicated by reference numeral 80. As illustrated, the guide surface 80 extends beyond the forward end of 14 and includes a forward edge 81 having a generally concave shape 84 lying between a pair of curved projections 85a and 85b. As best seen in FIG. 9, the anterior guide surface has a center line 87 which bisects the concave indentation 84 and the forward edge 81. In addition, the forward end 14 of the guide tube has a center line 89 which is offset laterally from the center line 87. As is known, the distal tip of the endotracheal tube 70 is normally beveled, with the bevel being indicated by reference numeral 91, looking down on the tube from above in FIGS. 10 and 11. If the center lines of the forward end 14 and the anterior guide surface of either of the above-described embodiments were co-linear, the engagement of the hyo-epiglottic ligament would result in an alignment between the beveled end 92 and the opening between the vocal cords 93, in the larynx, as illustrated in FIG. 10. In FIG. 10, the tip of the bevel 92 is offset from the center of the opening between the vocal cords 93, which might result in the bevel tip snagging on a vocal cord, preventing its entrance into the trachea. On the other hand, with the offset between center lines illustrated in FIG. 11, the distal end of the tube 70 is aligned with the center line of the forward end 14. However, the tip 92 of the bevel is now aligned substantially with the center line of the guide surface, and therefore with the center line of the vocal cord opening 93 in the larynx. This alignment increases the likelihood of the bevel tip 92 entering and guiding the distal end of the endotracheal tube 70 through the vocal cords and into the trachea.

The guide and insertion technique described above allows an endotracheal tube to be inserted "blind" relatively easily and dependably. The technique does not require potentially damaging movement of a patient's neck or direct observation of the larynx, which may be obscured through blood, vomitus, or other foreign matter which may be in the pharynx of trauma and cardiac arrest victims. Thus a tube can be inserted relatively quickly and reliably into the trachea to secure a patient's airway and assure adequate ventilation.

Figure 12:
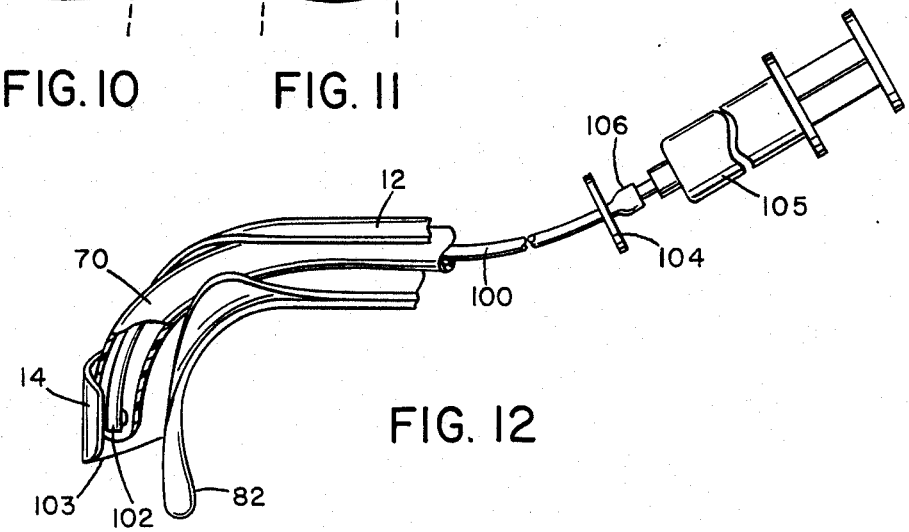
FIG. 12 is an illustration of a small tube inserted in the endotracheal tube for introducing a local anesthetic during intubation.

A small catheter 100, such as is llustrated in FIG. 12, may be provided to extend from the rear to the forward end of the guide, with a nozzle 102 at its forward end 103. A slidable stop 104 retains the proximal end of the catheter 100 at the rear end of the tube 12. This can be used with a syringe 105 of local anesthetic attached to the rear end 106 of the catheter 100. The catheter 100 is fed into the tube 70, and the guide, with the tube 70 in place, is advanced into a patient's throat. When the anesthetic is released into the catheter, it sprays ahead of the guide out the nozzles to anesthetize the tongue and larynx with local anesthetic. This can aid in inserting the guide and endotracheal tube in patients who are awake.

Although a preferred embodiment of the invention has been described above by way of example, it will be understood by those skilled in the field that modifications may be made to the disclosed embodiment without departing from the scope of the invention, which is defined by the appended claims.

I claim:

1. A tracheal intubation guide for assisting in insertion of a tube into a patient's trachea, comprising:
    a tubular member having a curved forward end for insertion into the mouth and throat of a patient and for following the curvature of the rear end of the tongue, a rear end for projecting out through the mouth of the patient, and a through bore for receiving an endotracheal tube; and
    an anterior guide surface means extending along at least part of the length of the tubular member to said forward end for guiding the tubular member over the tongue and into the throat of the patient to a position above the opening into the larynx, the guide surface means being curved to follow the curvature of the forward end of the tube and having a leading edge comprising a concave, linear indentation means for engaging the front of the epiglottis and fitting transversely over the hyo-epiglottic ligament with the center of the indentation seated directly on top of the hyo-epiglottic ligament to act as a stop preventing further insertion of the guide, and the opposite sides of the indentation means comprising means for engaging one on each side of the ligament to center the leading edge relative to the mid-line of the vallecula.

2. The guide as claimed in claim 1, in which the guide surface means is a flat strip of generally J-shape.

3. The guide as claimed in claim 1, in which the leading edge of the guide surface means includes a pair of rollers mounted on it having opposed surfaces defining the said concave shape, the pair of rollers comprising means for sliding the guide surface over the tongue and for seating over the hyo-epiglottic ligament.

4. The guide as claimed in claim 1, in which the anterior guide surface means is unbroken and the concave indentation means is formed between a pair of curved projections on said leading edge and is shaped to fit closely over the convex contour of the hyo-epiglottic ligament.

5. The guide as claimed in claim 1, wherein the guide surface means has a plurality of rollers for guiding the guide surface over the surface means of a tongue as the guide is inserted through the mouth and throat of a patient.

6. The guide as claimed in claim 1, wherein the tubular member has open portions extending along its length.

7. The guide as claimed in claim 6, wherein the open portions comprise a serpentine cut-out extending along the length of the tubular member.

8. The guide as claimed in claim 1, wherein the guide surface means has a forward end projecting outwardly from said forward end of the tubular member.

9. The guide as claimed in claim 1, wherein the tubular member has a handle portion at its rear end for gripping by an operator when inserting the guide into a patient's throat.

10. The guide as claimed in claim 9, wherein the handle portion has a thumb indentation for location of an operator's thumb to align the tubular member with an operator's hand.

11. A method of inserting a tube into a patient's trachea, comprising the steps of:
    inserting a tracheal intubation guide having a curved anterior guide surface means into the patient's mouth so that the guide surface follows the rear surface of the tongue into the throat, the guide surface means having a leading edge comprising a concave indentation means and the guide comprising a tubular member for receiving an endotracheal tube;
    advancing the guide until the concave indentation means engages the front of the epiglottis and fits over the midline of the hyo-epiglottic ligament;
    detecting accurate positioning of the guide by palpating the sides of the neck above the hyoid bone to determine whether any lateral edges of the guide are palpable;
    positioning of the guide until the lateral edges of the guide are not detected on palpation of the sides of the neck above the hyoid bone and the center of the indentation means is seated on top of the ligament to act as a stop preventing further insertion of the guide with the lateral edges of the indentation means engaging on each side of the ligament for centering the guide surface means relative to the mid-line of the vallecula;

elevating the epiglottis anteriorly to open the larynx; and guiding an endotracheal tube through the guide into the trachea.

12. The method as claimed in claim 11, in which the endotracheal tube is inserted through the tubular member towards its forward end prior to positioning of the guide in the throat, and including the additional step of removing the guide from the endotracheal tube via a serpentine cut-out extending along the length of the guide once the tube has been inserted in the trachea.

13. A tracheal intubation guide, comprising:
   a rigid tubular member with a curved forward end, a rear end, and a through bore connecting said rear end to said forward end;
   a continuous, serpentine opening in said tubular member extending on said through bore from said rear end to said forward end;
   a continuous, unbroken underside on said tubular member extending on said through bore from said rear end to said forward end; and
   an anterior guide surface means on said underside extending along at least part of the length of said tubular member, the guide surface means being curved to follow the curvature of said forward end and including a leading edge with concave means for engaging the front of the epiglottis and seating over the hyo-epiglottic ligament.

14. The tracheal intubation guide of claim 13 wherein said anterior guide surface means has a center line which substantially bisects said concave means and said tubular member is laterally offset from said center line.

15. The tracheal intubation guide of claim 14 wherein said anterior guide surface means is unbroken and said concave means is a concave indentation formed between a pair of curved projections on said leading edge.

16. A tracheal intubation apparatus, comprising:
   a tracheal intubation guide, including:
      a rigid tubular member with a curved forward end, a rear end, and a through bore connecting said rear end to said forward end;
      a continuous, serpentine opening in said tubular member extending on said through bore from said rear end to said forward end; and
      an anterior guide surface means on said underside extending along at least part of the length of said tubular member, the guide surface means being curved to follow the curvature of said forward end and including a leading edge comprising a concave indentation means having a center at the mid-point of said leading edge and opposite lateral edges extending from the center of the indentation means the indentation means comprising means for engaging the front of the epiglottis and fitting transversely over the hyo-epiglottic ligament with the center of the indentation means seated directly on top of the hyo-epiglottic ligament to act as a stop preventing further insertion of the guide, and the respective opposite lateral edges engaging on each side of the ligament to center the surface relative to the mid-line of the vallecula;
   an endotracheal tube removably contained in said rigid tubular member; and
   a tube in said endotracheal tube for conducting a local anesthetic from said rear end and emitting said local anesthetic at said forward end.

17. A tracheal intubation guide for assisting in insertion of a tube into a patient's trachea, comprising:
   a tubular member having a curved forward end for insertion into the mount and throat of a patient and for following the curvature of the rear end of the tongue, a rear end for projecting out through the mouth of the patient, and a through bore for receiving an endotracheal tube;
   an anterior guide surface means extending along at least part of the length of the tubular member to said forward end for guiding the tubular member over the tongue and into the throat of a patient to a position above the opening to the larynx, the guide surface means being curved to follow the curvature of the forward end of the tube and having a leading edge of concave shape for engaging the front of the epiglottis and seating over the hyo-epiglottic ligament; and
   the anterior guide surface means having a center line which substantially bisects said concave means, said tubular member being laterally offset from said center line.

18. A tracheal intubation guide for assisting in insertion of a tube into a patient's trachea, comprising:
   a tubular member having a curved forward end for insertion into the mouth and throat of a patient and for following the curvature of the rear end of the tongue, a rear end for projecting out through the mouth of the patient, and a through bore for receiving an endotracheal tube; and
   an anterior guide surface means extending along at least part of the length of the tubular member to said forward end for guiding the tubular member over the tongue and into the throat of the patient to a position above the opening to the larynx, the guide surface means being curved to follow the curvature of the forward end of the tube and having a leading edge comprising a concave indentation means shaped to fit closely over the convex contour of the hyo-epiglottic ligament, said leading edge having a pair of bulbous projections at its outer edges, one on each side of the concave indentation means.

* * * * *